United States Patent [19]

Kassis et al.

[11] Patent Number: 5,094,835
[45] Date of Patent: Mar. 10, 1992

[54] DIAGNOSIS OF TUMORS WITH 5-($^{123}$I)IODO-2'-DEOXYURIDINE

[75] Inventors: Amin I. Kassis, Chestnut Hill; S. James Adelstein, Waban, both of Mass.

[73] Assignee: The President and Fellows of Harvard College, Cambridge, Mass.

[21] Appl. No.: 651,785

[22] Filed: Feb. 7, 1991

Related U.S. Application Data

[62] Division of Ser. No. 502,759, Mar. 30, 1990, Pat. No. 5,077,034.

[51] Int. Cl.$^5$ .............................................. A61K 49/02
[52] U.S. Cl. ........................................ 424/1.1; 424/9
[58] Field of Search ...................................... 424/1.1, 9

[56] References Cited

PUBLICATIONS

Mercer, J. R. et al., "Synthesis and Tumor Uptake of . . . Uracils", *J. Med. Chem.*, 32, 1989, pp. 1289-1294.
Robins et al., "Iodine-123-Iododeoxyuridine: . . . ", *J. Nucl. Med. Biol.*, vol. 8, 1981, pp. 53-63.

*Primary Examiner*—John S. Maples
*Attorney, Agent, or Firm*—Allegretti & Witcoff, Ltd.

[57] ABSTRACT

A method for the treatment and diagnosis of tumors is disclosed. This method comprises the direct administration of an effective anti-tumor amount of a radiohalogenated pyrimidine nucleoside such as $^{123}$IUdR to the affected site.

1 Claim, 5 Drawing Sheets

DIAGNOSIS OF TUMORS WITH 5-($^{123}$I)IODO-2'-DEOXYURIDINE

This invention was supported under NIH Grant RO1-CA 15523 and the U.S. Government has certain rights to the invention.

This application is a division of application Ser. No. 07/502,759, filed Mar. 30, 1990, now U.S. Pat. No. 5,077,034.

BACKGROUND OF THE INVENTION

The present invention relates to methods for the treatment of tumors in mammals by injecting or infusing an effective anti-tumor amount of radiohalogenated pyrimidine nucleosides such as 5-halo-2'-deoxypyrimidine and typically 5-iodo-2'-deoxyuridine in a pharmaceutically acceptable vehicle directly to the affected site. These nucleosides include for example, 5-[$^{123}$I $^{125}$I]iodo-2'-deoxyuridine which are hereinafter abbreviated as $^{123}$IUdR or $^{125}$IUdR.

The present invention also includes within its scope methods for diagnosing tumors and or predicting their progress by intratumor administration of $^{123}$IUdR or $^{125}$IUdR.

It has been demonstrated that the Auger effect accompanying the decay of iodine-125[$^{125}$I] or iodine-123[$^{123}$I] is extremely toxic to cultured mammalian cells when these are incorporated into nuclear DNA in the form of the corresponding thymidine analog i.e., 5-[$^{123}$I/$^{125}$I]iodo-2'-deoxyuridine [$^{123/125}$IUdR]. Further in vitro studies indicated that these and other Auger electron emitters have also shown the ineffectiveness of this decay mode when it occurs at a distance from the nuclear DNA.

Tumors of the central nervous system are estimated to cause the death of 90,000 patients in the United States each year. One-fourth of the annual 4 billion dollar cost for care of cancer patients in the United States is allocated for patients inflicted with such neoplasms. The incidence of secondary neoplasms is much greater than that of primary neoplasms. In the young patient [3-12 years], CNS tumors comprise the most common group of solid tumors and account for 20% of all pediatric neoplasms. These tumors are different in histology and behavior from those seen in adults [50-70 years].

Gliomas comprise about 60% of all primary CNS tumors and they constitute the bulk of the intrinsic intraparenchymal tumors of both brain and spinal cord. These tumors arise from distinct types of glial cells. Regardless of the location of the malignant glioma, the prognosis has not changed greatly in the last 20 years. Following treatment, recurrence is usually observed within 6 months and 80% of these patients die within 6 to 12 months. Efforts to improve prognosis for this malignancy have included, among others, the development of microsurgical techniques; improvement in drug delivery systems; high dose radiotherapy alone or in combination with nitrosoureas such as N,N-bis(2-chloroethyl)-N-nitrosourea [BCNU]; radiotherapy trials of implanted radiation sources [brachytherapy] with seeds of iodine-125, iridium-192, or gold-198; local arterial infusions of BCNU or cisplatin; intrathecal administration of chemotherapeutic agents; use of interferon; administration of radiosensitizers such as IUdR and bromodeoxyuridine [BrUdR]; and most recently the use of $^{131}$I-labeled m-iodobenzylguanidine. Despite these therapeutic approaches, progress in the therapy of high-grade brain tumors, particularly glioblastoma multiform, has been modest at best. The fundamental problem lies in the impossibility of total removal or effective sterilization e.g., radiation, chemotherapy, etc. of the tumor. This impass motivates the search for alternate treatment modalities that will show preferential uptake and selective killing of these tumors.

For a number of years, the scientific and medical communities have been continually exploring the possibility of using radionuclides for cancer therapy. The use of sealed radioactive sources [e.g., radium needles and capsules] is now commonplace. However, with the exception of a select number of applications, the hopes of employing unsealed sources for the radiotherapy of a neoplastic disease remain largely unrealized. The problem has two components: (a) the paucity of appropriate radionuclides, and (b) the scarcity of carrier molecules that can (i) bring the radionuclide into the vicinity of cancerous cells and (ii) achieve high therapeutic ratios between tumor cells and normal tissues.

DESCRIPTION OF THE PRIOR ART

The biological toxicity of internally deposited radionuclides can be attributed to radiation-induced ionizations and excitations, nuclear recoil, chemical transmutations, and local charge effects. Gamma and x-ray photons, energetic negatrons and positions have (i) a range of action equivalent to many cell diameters, (ii) are characterized by a low linear energy transfer [LET] and oxygen-dependent biological effects. On the other hand, radionuclides that decay by electron capture [EC] and/or internal conversion [IC] demonstrate an Auger effect in which extremely low energy [<1 KeV], short range electrons are produced which dissipate their energy typically within nanometer distances from the decay site. Consequently, the biological toxicity of these radionuclides resembles that of high LET radiations and is critically dependent on their intranuclear localization. Furthermore, the oxygen enhancement ratios [OER] obtained following their decay are smaller than those seen with x-irradiation and energetic particles.

The Auger-electron-emitting radionuclide investigated most extensively is iodine-125. Because of its predominant [93%] IC decay following EC, this radionuclide is a prolific emitter of Auger electrons [mean of 20 per decay]. The electrons most frequently produced dissipate their energy in the immediate vicinity of the decaying atom and deposit $10^5$-$10^9$ rad/decay within 20-to-60-nanometer spheres around the decaying atom (20-22). The radiotoxicity of this Auger electron emitter was demonstrated following the in vitro incorporation of the thymidine [TdR] analog $^{125}$IUdR into the DNA of dividing mammalian cells.

5-Iodo-2'-deoxyuridine is a thymidine analog in which the 5-methyl group of thymidine (TdR) is replaced by iodine. The preparation of this compound as well as the iodinated $^{123}$I and $^{125}$I are fully described in U.S. Pat. No. 4,851,500 the teachings of which are incorporated herein by reference.

Briefly, 2'-deoxyuridine [0.50 g, 2.20 mmol] is dissolved in 2 ml water and the solution is heated to 50° C. To this solution, mercuric acetate [0.74 g, 2.32 mmol] in 3 ml of water is added. The reaction is allowed to proceed for 2.5 h at 50° C., the vial cooled down to 40° C., and sodium chloride [0.32 mg, 5.45 mmol] in 1 ml of water is added. The reaction mixture is stirred for 1 h, and the suspension is filtered, washed and dried.

To 6 mg [8.6 μmol] of the thus prepared 5-chloro-2'-deoxyuridine, 4 mg of Iodogen [9.3 μmol] and sodium [$^{123}$I/$^{125}$I]iodide [1-10 mCi] in 0.3 ml of water are added. The mixture is stirred in a closed 2-ml reaction vial at room temperature for 2 h, filtered through a 0.22 μm Millex filter, and injected into the HPLC [C$_{18}$ column]. Fractions from the peak with a retention time [R$_T$] of 7.1 min [corresponding to that of an authentic cold IUdR sample] are pooled, the eluant [H$_2$O/CH$_3$OH,80/20 by volume] evaporated, and the $^{123}$IUdR or $^{125}$IUdR resuspended in saline and sterilized e.g., by filtration, prior to administration into the mammals.

Despite the fact that various pharmaceuticals that exhibit high in vitro toxicity to mammalian cells have been identified over the years, none of these have demonstrated any "magic bullet" characteristics in vivo. To facilitate targeting to tumors, investigators have relied on the direct introduction of the therapeutic/diagnostic agents either into the target area or into an arterial blood supply that immediately precedes the target. Inherent to the absolute success of such approaches are four main assumptions:

1. the target is approximately within an area that can be easily accessed;
2. once within the vicinity of the tumor-containing tissues, the agent (a) freely diffuses throughout all the tissues, (b) is innocuous outside the cell, and (c) is selectively taken up (passively/actively) and indefinitely retained by each and every cancerous cell but not by noncancerous cells;
3. once the agent has diffused out of the target area, it must either be converted quickly into an inactive, i.e., nontoxic, form and/or excreted be from the body;
4. the biologic behavior of the agent is not altered by repeated injection, i.e., it lends itself to repeat/continuous injections.

SUMMARY OF THE INVENTION

We have found that IUdR is the agent that meets most of the above requirements when it is injected/infused intracerebrally, intraventricularly, or intraarterially. Being a low-molecular-weight molecule, it diffuses readily within tissues when radiolabeled with an Auger electron emitter i.e., $^{123}$I, $^{125}$I, $^{124}$I, $^{131}$I, $^{77}$Br, $^{80m}$Br, ($^{123}$I or $^{125}$I being preferred) it is innocuous outside the cell and ineffective at killing cells when within the cytoplasm; it is taken up selectively by dividing cancerous cells located within nondividing cells of the CNS for the most part, it is indefinitely retained following DNA incorporation; by far, the majority of the cells within the CNS are nondividing and will not incorporate IUdR into their DNA; most of the IUdR that will escape from the CNS will be catabolized/dehalogenated rapidly [t$_\frac{1}{2}$ of min] and thus will not incorporate into the DNA of distant noncancerous dividing cells; and being a small molecule, IUdR will not induce an antibody response and as such will lend itself to repeated injections/continuous infusion.

Accordingly, the present invention relates to methods for the treatment of tumors which are directly accessible by injecting or infusing an effective anti-tumor amount of a radiohalogenated pyrimidine nucleosides in a pharmaceutically acceptable vehicle directly to the affected site. These radiohalogenated compounds include for example, UdR labelled with $^{123}$I, $^{125}$I, $^{124}$I, $^{77}$Br, $^{80m}$Br, and in particular radioiodinated pyrimidine nucleoside, such as 5-iodo-2'-deoxyuridine. These methods as well as the pharmaceutical composition will become more apparent from the following detailed description.

DETAILED DESCRIPTION OF THE INVENTION

Figure 1:
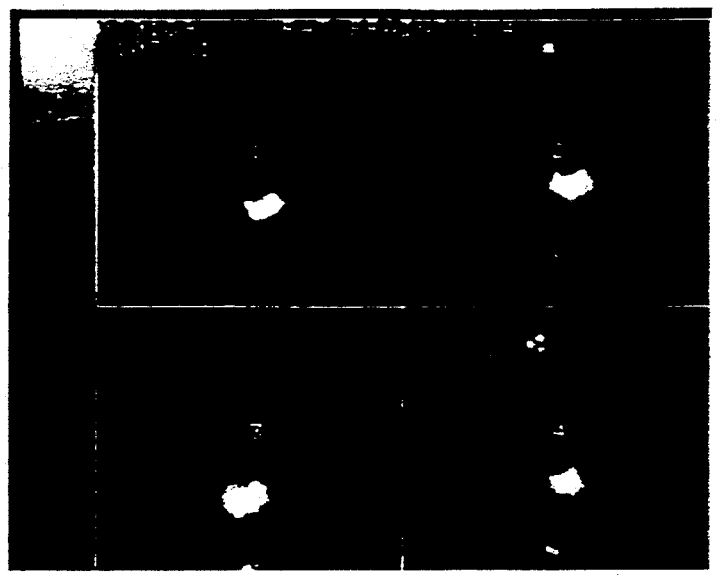

According to the present invention, the selected radionucleoside e.g., $^{123}$IUdR and $^{125}$IUdR prepared according to the method of U.S. Pat. No. 4,851,520 is dissolved in a pharmaceutically acceptable vehicle such as sterile normal saline yielding an effective diagnostic or therapeutic amounts per dose unit. Generally speaking, each dose contains about 1-5 mCi (diagnosis) and 10-500 mCi (therapy) of the selected compound.

The resulting composition is administered as follows:

1. For tumors of the central nervous system: Following initial direct intracerebral administration single/multiple injection or infusion of radiolabeled IUdR is administered directly into the tumor site; or direct intraventricular administration single/multiple injection or infusion of the radiolabeled IUdR; or intracarotid administration followed by single/multiple injection or infusion of radiolabeled IUdR; or direct intrathecal administration followed by single/multiple injection or infusion; or the above four routes following the administration of other cytotoxic agents such as fluorodeoxyuridine and/or methotrexate or similar anti metabolities to enhance IUdR uptake by tumor cells.
2. In prostate cancer: Following initial direct intratumor administration, single/multiple injection or infusion is administered.
3. For tumors within the stomach wall: The composition is administered directly into the lumen of the stomach following intubation, or following direct intratumor administration, single/multiple injection or infusion is administered.
4. For cancers within the colon wall: The composition is administered directly into the lumen of the colon or following direct intratumor administration, single/multiple injection or infusion is administered.
5. For tumors within the bladder wall: The composition is administered directly into the bladder following intubation, or following direct intratumor administration, single/multiple injection or infusion is administered.
6. In ovarian cancers: Following initial intraperitoneal administration, single/multiple injection or infusion is administered.
7. In intrahepatic tumors: Following initial intraarterial administration via a hepatic artery catheter, single/multiple injection or infusion is administered.
8. Any tumor that is accessible via direct intratumor, intraarterial, intraventricular, intrathecal, intralymphatic, intraorgan containing tumor, intratissue containing tumor, intracavitary e.g., pulmonary, positioned, bone marrow, injection i.e., single or multiple.

The pharmaceutically acceptable compositions for administration of the $^{123}$IUdR $^{125}$IUdR for intra-cerebral, intraventricular, intra-carotid or intra-tumor maybe formulated by methods known to the pharmacist art, using suitable non-toxic, parenterally acceptable solvent such as normal saline, Ringer's solution and formulating into sterile dosage forms for these administrations.

It is to be understood that the specific dose level and the particular dosage regimen for any particular patient will depend upon a variety of factors including for example, the age, body weight, sex and severity of the particular condition of the host undergoing therapy. The dosage regimen therefore needs to be individualized by the clinician based on clinical response.

In order to illustrate further the practice of this invention, the following examples are included:

EXAMPLES

$^{123}$IUdR in the Scintigraphic Diagnosis of Brain Tumors

Exponentially growing 9L gliosarcoma cells were stereotactically implanted into the right caudate nucleus of 3-week-old CDF [Fisher 344] rats. Briefly, the rats were anesthetized via an i.p. injection of ketamine [40 mg/kg] and xylazine [10 mg/kg] and placed in a small animal stereotactic frame [Kopf Instruments]. A sagittal incision through the scalp exposed the skull and a small burr hole was made 1.3 mm posterior and 4 mm to the right of the bregma. Tumor cells [$2 \times 10^4$/10 $\mu$l PBS], were then injected slowly [within 30 sec] at a depth of 4 mm using a 701 Hamilton syringe. The needle was left in place for 1 min and then withdrawn slowly. The hole was plugged with bone wax and the incision closed. The animals developed sizable tumors [0.1–4 mm in diameter] within 16 days and died by day $20 \pm 2$. Control animals were sham-operated with the injection of normal saline.

5-Iodo-2'-deoxyuridine was simultaneously radiolabeled with a mixture of [$^{123}$I/$^{125}$I]sodium iodide by the method according to U.S. Pat. No. 4,851,500. Briefly, 2'-deoxyuridine [0.5 g, 2.20 mmol] was dissolved in 2 ml water and the solution is heated to 50° C. To this solution, mercuric acetate [0.74 g, 2.32 mmol] in 3 ml of water was added. The reaction was allowed to proceed for 2.5 h at 50° C., the vial cooled down to 40° C., and sodium chloride [0.32 mg, 5.45 mmol] in 1 ml of water was added. The reaction mixture was stirred for 1 h, and the suspension was filtered, washed and dried.

To 6 mg [8.6 $\mu$mol] of the prepared 5-chloro-2'-deoxyuridine, 4 mg of Iodogen [9.3 $\mu$mol] and sodium [$^{123}$I/$^{125}$I]iodide [1–10 mCi] in 0.3 ml of water were added. The mixture was stirred in a closed 2-ml reaction vial at room temperature for 2 h, filtered through a 9.22 $\mu$m Millex filter, and injected into the HPLC [$c_{18}$ column]. Fractions from the peak corresponding to that of an authentic cold IUdR sample [retention time = 7.1 min] were pooled, the eluant [H$_2$O/CH$_3$OH, 80/20 by volume] evaporated, and the $^{123}$IUdR/$^{125}$IUdR mixture resuspended in saline and sterilized by Millipore filtration.

$^{123}$IUdR [150–400 $\mu$Ci $^{123}$IUdR in 10 $\mu$l] was stereotactically injected directly into the brain 15 to 17 days post tumor or saline inoculation using the same coordinates used to introduce the tumor cell or normal saline inoculum. Scintigraphic images [$^{123}$IUdR] were obtained 1 to 38 h post $^{123}$IUdR injection using a gamma camera [Starcam] equipped with a medium energy collimator [anterior views, $128 \times 128$ matrix, 2.67 magnification, 10 min acquisition]. Biodistribution of radioactivity was determined 40 h after $^{123}$IUdR injection. The following samples and tissues were obtained, rinsed, blotted, weighted, and their $^{123}$I radioactive content determined in a gamma counter: tumor-containing or sham-operated right brain, left brain, frontal lobes, skin, muscle, small intestine, large intestine, spleen, liver, kidney, heart, lung, right skull, left skull, bone, thyroid, bladder, urine, stomach, stomach contents, and blood. The frontal lobes were dissected away from the rest of the brain and counted separately. A coronal section of the brain was made through the plane of the injection site, and one-half of this tissue was immediately frozen in isopentane using liquid nitrogen for later sectioning [6 $\mu$m] for histopathology and autoradiography. Examination of the other half indicated that in the few instances where the tumor mass was macroscopically visible, its delineation from the normal brain tissue was difficult. For these reasons, this part of the brain was cut in half through the midline to obtain a "right brain" sample [containing the tumor site and/or injection site], and a "left brain" sample [uninjected side representing the activity in the contralateral "normal" brain].

The scintigraphic images obtained 1 h after $^{123}$IUdR injection showed activity in the head of both tumor-bearing [n = 16] and sham-operated control [n = 8] animals. Activity in the stomach and the bladder was also evident suggesting the rapid dehalogenation and excretion of free iodine. No activity was seen in the thyroid [0.1% potassium iodide solution had been added to the drinking water 48 h prior to the administration of radioactive IUdR]. Images obtained at subsequent intervals [12–38 h] demonstrated clearance of the activity from the head of all control animals by 12 h [FIG. 1-1 and 1-3] and persistence of the activity within the same region in all tumor-bearing animals [FIG. 1-2 and 1-4]. Bladder and stomach activities were still observed in both groups [these radioactivities were mainly associated with the stomach contents and with urine, see FIG. 2].

Regions of interest were drawn around the head of all animals. Even 1 h after injection, the men counts per pixel in the tumor-bearing animals were at least twice that of the control animals. This ratio increased with time to a maximum of 3.8 by 38 h.

Figure 2:
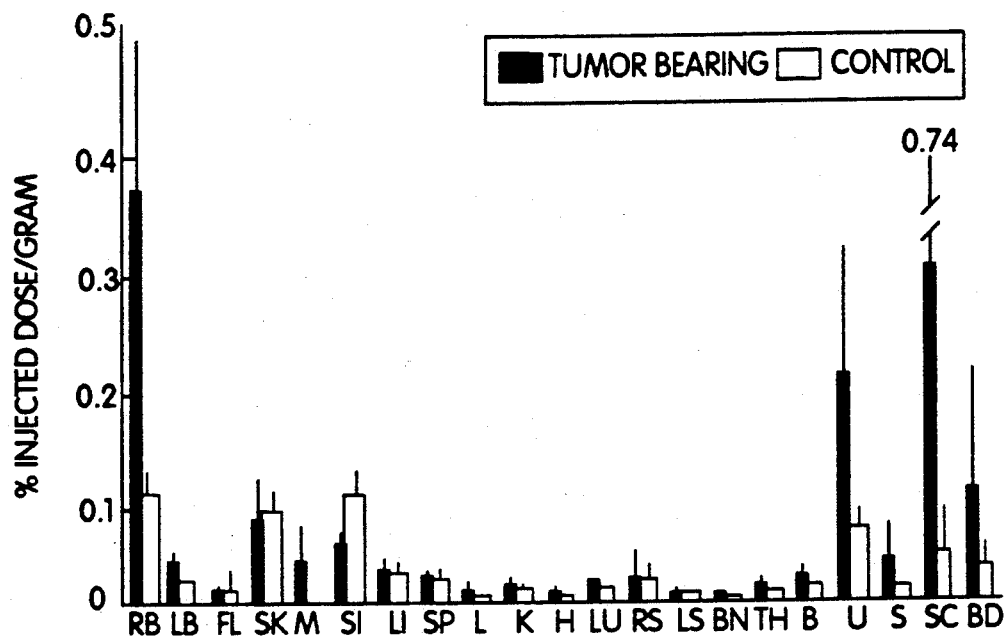

The biodistribution data [40 h after $^{123}$IUdR injection] indicated that samples obtained from the "left brain" [uninjected side] or the frontal lobes in tumor-bearing and control animals had similar amounts of activity [FIG. 2]. On the other hand, samples obtained from the "right brain" [injected side] in tumor-bearing animals contained $0.36 \pm 0.14\%$ of the injected dose per gram [%ID/g, mean$\pm$SD] as opposed to $0.09 \pm 0.02\%$ ID/g from the same side of the brain in sham-operated controls (P<0.05). Since a large proportion of the weighed "tumor" sample is, in fact, uninvolved brain tissue [some of the tumors were not visible macroscopically at the time of dissection, i.e., <0.5 mm in diameter], these % ID/g values underestimate the actual tumor uptake. This is further emphasized by the high uptake that was observed in two animals, one in which 12% of the ID was found to be associated with a tumor that could be precisely excised, and another in which 25% of the ID was found in a tumor that occupied a large portion of the "right brain" specimen. As suggested by the scintigraphic studies, the activity in all other normal tissues was low with the exception of the stomach and the bladder. However, examination of these organs indicated that the high activities observed were mainly associated with the stomach contents and with urine.

Figure 3:
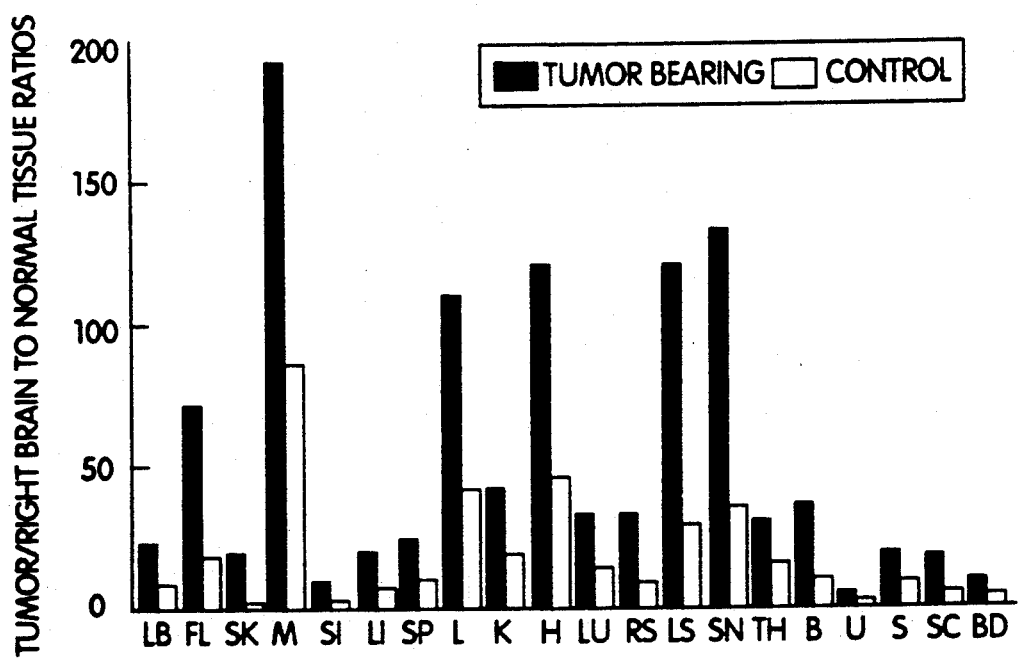
Figure 4:
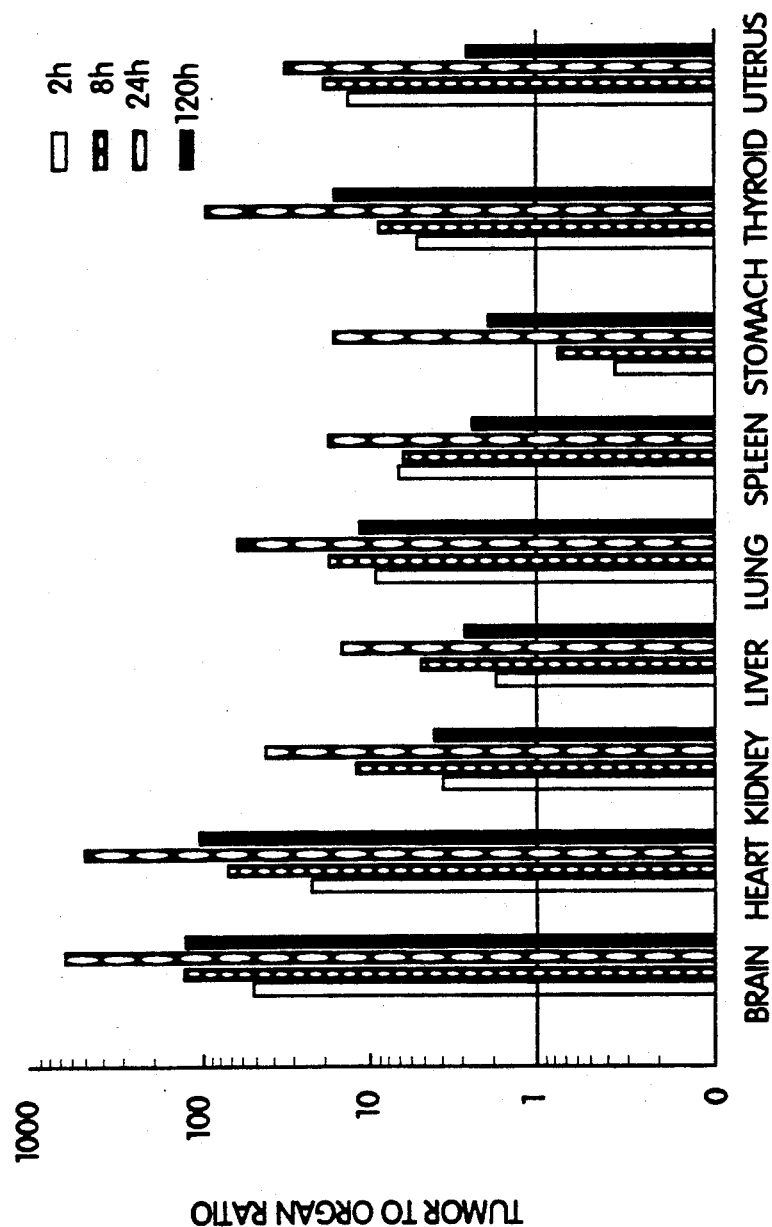

Using the biodistribution data shown in FIG. 2, tumor to normal tissue ratios were calculated and found to be equal to or greater than eight for all the tissues [FIG. 3]. Of particular interest, in the tumor-bearing animals right brain/left brain = 22, right brain/frontal lobes = 71, right brain/blood = 9. Again, much higher T/N ratios [range of 53 to 488] were obtained in an animal where the brain tumor mass was sufficiently large [about 3×4 mm] to be excised and where the radioactivity per gram of tumor could be accurately assessed:

II. Therapeutic Efficacy of $^{125}$IUdR and $^{123}$IUdR in Ovarian Tumors

1. Intraperitoneal Injection of $^{125}$IUdR leads to High Tumor to Nontumor Ratios The murine ovarian tumor (MOT) used in these experiments arose spontaneously in the ovary of a C3H mouse and is maintained in our laboratories by serial intraperitoneal [i.p.] transplantation in female C3HeB/-FeJ mice. We have examined the appropriateness of the i.p. route for IUdR administration as a means to (i) bypass the rapid intrahepatic dehalogenation of this agent, and (ii) obtain high tumor to nontumor ratios. In these experiments, mice were injected with $10^6$ tumor cells 24 h prior to the i.p. administration of $^{125}$IUdR [5 injections, 4 h apart]. Biodistribution studies 24 h following the last $^{125}$IUdR injection have shown extremely favorable tumor to non-tumor ratios [FIG. 4]. Tumor-to-normal-tissue ratios derived from the biodistribution results ranged from 20 for organs with actively proliferating cells (for example uterus, intestine, stomach) to over 400 for organs with nondividing cells (brain, heart).

Figure 5:
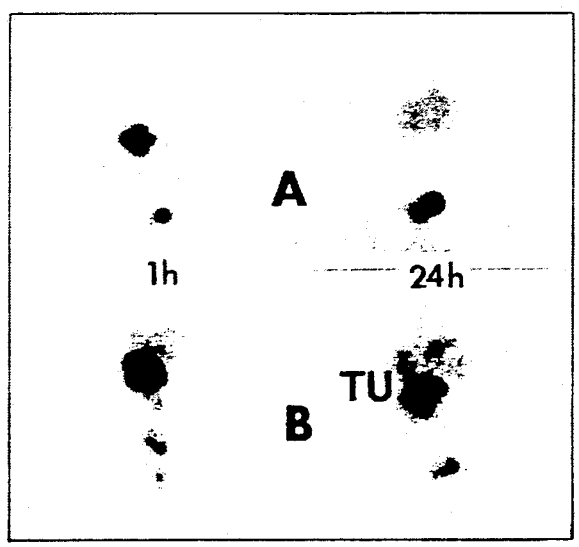

Analogous results were obtained from the scintigraphic images acquired 1, 2, 16 and 24 hr following a single injection of 300 μCi $^{123}$IUdR [FIG. 5]. At 1 h post radiopharmaceutical injection, focal localization of radioactivity was observed in the abdomen of both tumor-bearing mice and control animals. However, at later time points, the focal area of abdominal activity persisted only in MOT-bearing mice while it cleared from the abdomen of animals without tumor, confirming biodistribution results.

2. $^{125}$IUdR Is an Effective Antineoplastic Agent In A Mouse Ascites Tumor

The tumor used in these experiments is the same murine ovarian tumor described above. We have determined the median survival of mice after i.p. challenge with various tumor cell inocula. The results indicate that the median survival of these mice is proportional to the number of tumor cells inoculated into the mice.

The relatively long survival of tumor-bearing mice facilitates quantitative evaluation of tumor cell killing after treatment with $^{125}$IUdR and can be used to calculate a cellular survival fraction. We have, therefore, studied tumor cell survival as a function of the dose of $^{125}$IUdR administered i.p. at 4 h intervals beginning 24 h after tumor cell i.p. inoculation [$10^5$–$10^6$ cells]. Because IUdR dehalogenates rapidly in vivo, potassium iodide is added to the animals' drinking water to block thyroid uptake of the released radionuclides.

Figure 6:
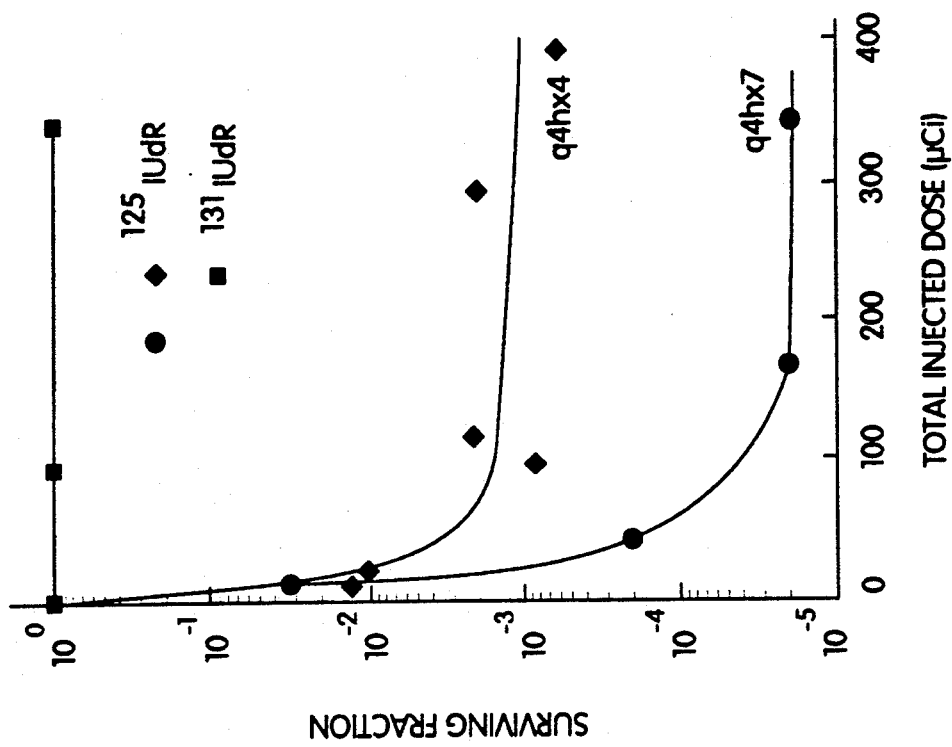

When mice are treated with four doses of $^{125}$IUdR at 4-h intervals and the survival fraction plotted as a function of the dose per treatment, a rapid decrease in the tumor cell survival fraction [$10^{-3}$] is observed at doses of 20 μCi per treatment with the curve being flat at higher levels [FIG. 6]. When seven consecutive injections of $^{125}$IUdR are given, a similar steep reduction in tumor cell survival is also observed; the plateau in this regimen occurs at a survival fraction of $10^{-5}$. Finally, treatment with equivalent doses of IUdR radiolabeled with $^{131}$I [a negatron emitter whose decay is not associated with any significant yield of Auger electron emissions] does not result in any decrease in survival.

3. $^{123}$IUdR Is An Effective Antineoplastic Agent In A Mouse Ascites Tumor

Figure 7:
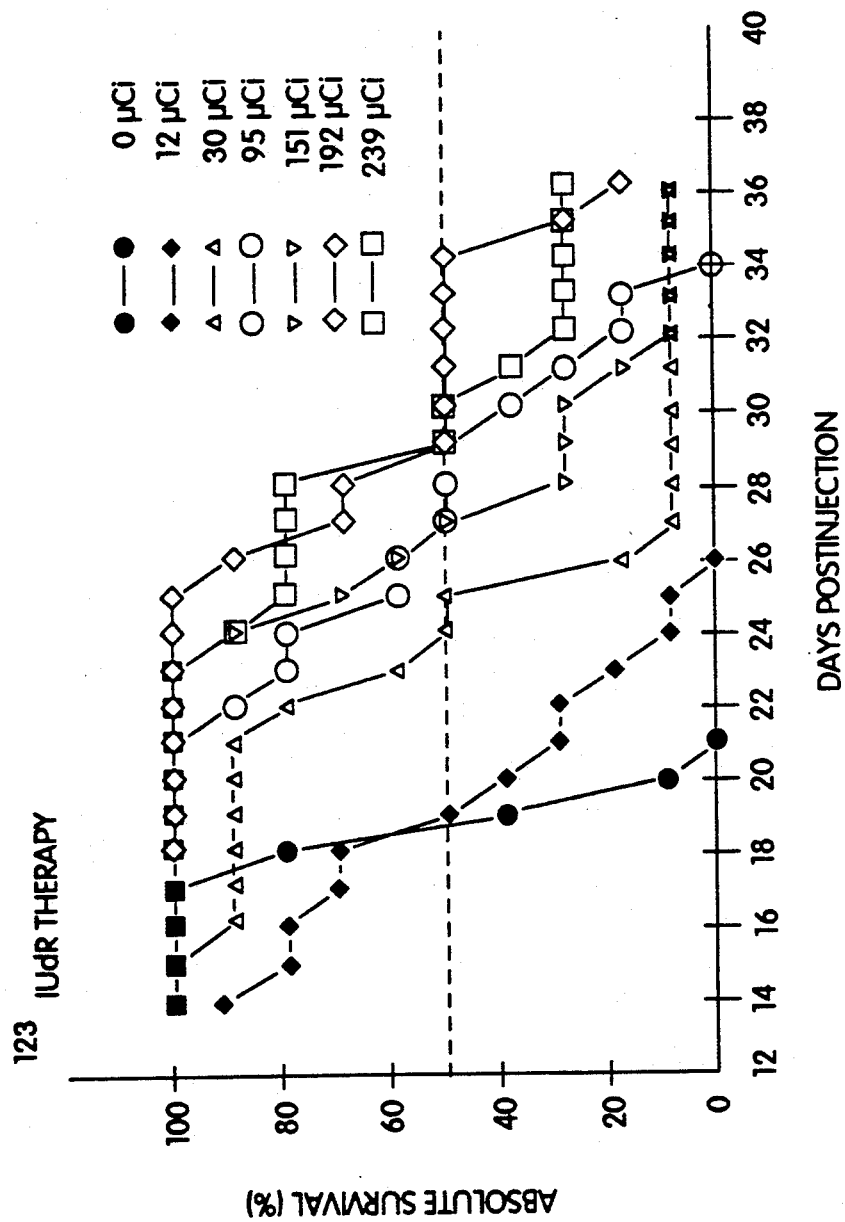
Figure 8:
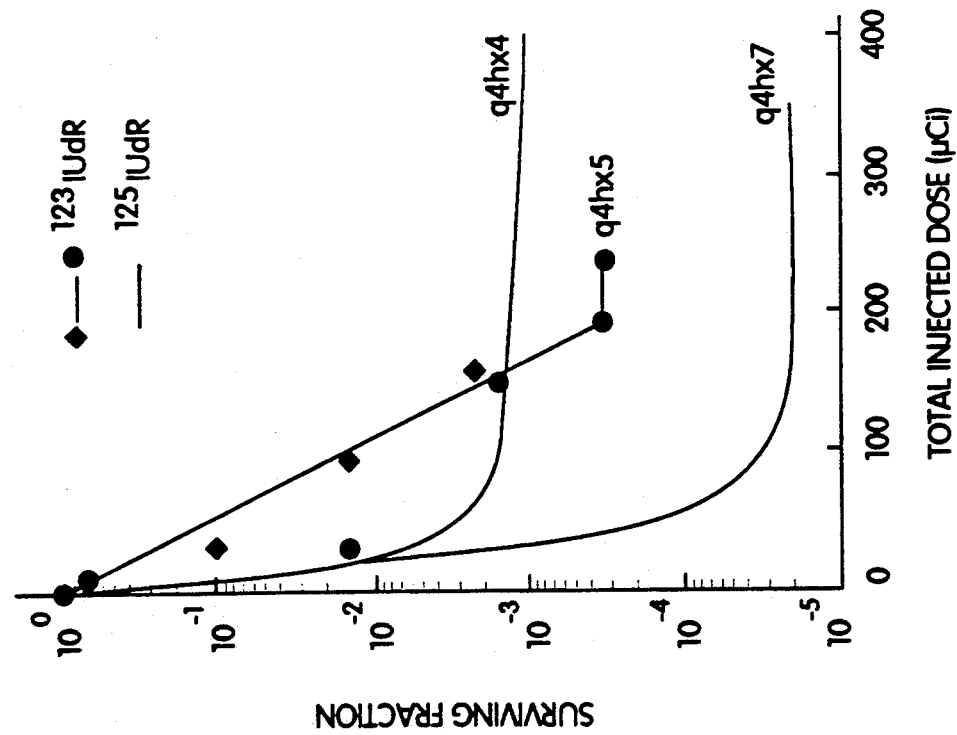

Recently, we have repeated the experiments described above using $^{123}$IUdR [5 i.p. injections, 4 h intervals, 24 h post i.p. tumor inoculation]. Our results indicate that the incorporation of this Auger electron emitter into the DNA of these tumor cells also prolongs median survival of the tumor-bearing animals [FIG. 7] in a dose-dependent fashion. When the survival fraction of tumor cells is plotted as a function of dose, an exponential decrease is obtained similar to that observed with the $^{125}$IUdR data [FIG. 8].

What is claimed is:

1. A method for the diagnosis of tumors in a live mammal which comprises the direct injection of 1–5 mCi of 5-($^{123}$I)iodo-2'-deoxyuridine in a pharmaceutically acceptable vehicle into the tumor, and thereafter imaging the tumor scintigraphically.

* * * * *